(12) United States Patent
Mazar et al.

(10) Patent No.: US 8,700,172 B2
(45) Date of Patent: Apr. 15, 2014

(54) IMPLANTABLE MEDICAL DEVICE HAVING LONG-TERM WIRELESS CAPABILITIES

(75) Inventors: Scott T. Mazar, Inver Grove Heights, MN (US); Yatheendhar D. Manicka, Woodbury, MN (US)

(73) Assignee: Cardiac Pacemakers, St. Paul, MN (US)

( * ) Notice: Subject to any disclaimer, the term of this patent is extended or adjusted under 35 U.S.C. 154(b) by 1158 days.

(21) Appl. No.: 12/151,400

(22) Filed: May 6, 2008

(65) Prior Publication Data

US 2008/0211665 A1  Sep. 4, 2008

Related U.S. Application Data

(62) Division of application No. 10/328,655, filed on Dec. 23, 2002, now Pat. No. 7,395,117.

(51) Int. Cl.
*A61N 1/08* (2006.01)

(52) U.S. Cl.
USPC ............................................. 607/60; 128/904

(58) Field of Classification Search
USPC .................. 607/60; 600/481, 509; 128/904
See application file for complete search history.

(56) References Cited

U.S. PATENT DOCUMENTS

| | | |
|---|---|---|
| 4,561,443 A | 12/1985 | Hogrefe et al. |
| 4,658,831 A | 4/1987 | Reinhard et al. |
| 4,681,111 A | 7/1987 | Silvian |
| 4,705,043 A | 11/1987 | Imran |
| 4,757,816 A | 7/1988 | Ryan et al. |
| 4,793,353 A | 12/1988 | Borkan |
| 4,809,697 A | 3/1989 | Causey, III et al. |
| 4,932,408 A | 6/1990 | Schaldach |
| 4,947,407 A | 8/1990 | Silvian |
| 4,969,464 A | 11/1990 | Callaghan et al. |
| 5,058,581 A | 10/1991 | Silvian |
| 5,081,987 A | 1/1992 | Nigam |
| 5,113,869 A | 5/1992 | Nappholz et al. |
| 5,117,825 A | 6/1992 | Grevious |
| 5,137,022 A | 8/1992 | Henry |
| 5,241,961 A | 9/1993 | Henry |
| 5,292,343 A | 3/1994 | Blanchette et al. |
| 5,331,966 A | 7/1994 | Bennett et al. |

(Continued)

FOREIGN PATENT DOCUMENTS

EP  0554955 A1  8/1993

OTHER PUBLICATIONS

"U.S. Appl. No. 10/328,655, Response filed Jan. 10, 2006 to Non-Final Office Action mailed Nov. 1, 2006", 12 pgs.

(Continued)

*Primary Examiner* — Tammie K Heller
(74) *Attorney, Agent, or Firm* — Schwegman, Lundberg & Woessner, P.A.

(57) ABSTRACT

A medical device is capable of utilizing a pervasive wireless communications network, such as a digital wireless telephone network, personal communication services network or pager network, to directly communicate with a host computer without the need for a repeater device. The device includes a sensor capable of measuring a body characteristic, such as temperature or electrical cardiac activity, and generates clinical data describing the measurement. The device also includes a wireless transmitter/receiver unit capable of establishing a communications link with a host computer over the long-range wireless network. The wireless transmitter/receiver unit is capable of delivering the measured clinical data to the host computer over the wireless network. The wireless transmitter/receiver unit can also periodically deliver status information regarding the operation of the implantable device to the host computer.

13 Claims, 9 Drawing Sheets

(56) References Cited

U.S. PATENT DOCUMENTS

| | | |
|---|---|---|
| 5,336,245 A | 8/1994 | Adams et al. |
| 5,350,411 A | 9/1994 | Ryan et al. |
| 5,381,798 A | 1/1995 | Burrows |
| 5,383,915 A | 1/1995 | Adams |
| 5,413,594 A | 5/1995 | Williams |
| 5,415,181 A | 5/1995 | Hogrefe et al. |
| 5,458,122 A | 10/1995 | Hethuin |
| 5,476,485 A | 12/1995 | Weinberg et al. |
| 5,481,262 A | 1/1996 | Urbas et al. |
| 5,509,927 A | 4/1996 | Epstein et al. |
| 5,522,865 A | 6/1996 | Schulman et al. |
| 5,549,654 A | 8/1996 | Powell |
| 5,626,630 A | 5/1997 | Markowitz et al. |
| 5,629,678 A | 5/1997 | Gargano et al. |
| 5,630,836 A | 5/1997 | Prem et al. |
| 5,674,249 A | 10/1997 | De Coriolis et al. |
| 5,683,432 A | 11/1997 | Goedeke et al. |
| 5,713,937 A | 2/1998 | Nappholz et al. |
| 5,720,770 A | 2/1998 | Nappholz et al. |
| 5,741,315 A | 4/1998 | Lee et al. |
| 5,743,267 A | 4/1998 | Nikolic et al. |
| 5,752,976 A | 5/1998 | Duffin et al. |
| 5,752,977 A | 5/1998 | Grevious et al. |
| 5,759,199 A | 6/1998 | Snell et al. |
| 5,766,232 A | 6/1998 | Grevious et al. |
| 5,769,876 A | 6/1998 | Silvian |
| 5,772,586 A | 6/1998 | Heinonen et al. |
| 5,774,501 A | 6/1998 | Halpern et al. |
| 5,791,342 A | 8/1998 | Woodard |
| 5,792,207 A | 8/1998 | Dietrich |
| 5,814,089 A | 9/1998 | Stokes et al. |
| 5,836,983 A | 11/1998 | Weijand et al. |
| 5,843,133 A | 12/1998 | Routh et al. |
| 5,843,139 A | 12/1998 | Goedeke et al. |
| 5,861,014 A | 1/1999 | Familoni |
| 5,861,018 A | 1/1999 | Feierbach |
| 5,862,803 A | 1/1999 | Besson et al. |
| 5,889,474 A | 3/1999 | LaDue |
| 5,899,928 A | 5/1999 | Sholder et al. |
| 5,899,931 A | 5/1999 | Deschamp et al. |
| 5,917,414 A | 6/1999 | Opplet et al. |
| 5,919,214 A | 7/1999 | Ciciarelli et al. |
| 5,935,078 A | 8/1999 | Feierbach |
| 5,944,659 A | 8/1999 | Flach et al. |
| 5,957,861 A | 9/1999 | Combs et al. |
| 5,999,857 A | 12/1999 | Weijand et al. |
| 6,083,248 A | 7/2000 | Thompson |
| 6,093,146 A | 7/2000 | Filangeri |
| 6,115,636 A | 9/2000 | Ryan |
| 6,141,584 A | 10/2000 | Rockwell et al. |
| 6,170,488 B1 | 1/2001 | Spillman, Jr. et al. |
| 6,185,452 B1 | 2/2001 | Schulman et al. |
| 6,200,264 B1 | 3/2001 | Satherley et al. |
| 6,203,495 B1 | 3/2001 | Bardy |
| 6,206,835 B1 | 3/2001 | Spillman, Jr. et al. |
| 6,208,894 B1 | 3/2001 | Schulman et al. |
| 6,213,942 B1 | 4/2001 | Flach et al. |
| 6,216,038 B1 | 4/2001 | Hartlaub et al. |
| 6,221,011 B1 | 4/2001 | Bardy |
| 6,223,083 B1 | 4/2001 | Rosar |
| 6,236,889 B1 | 5/2001 | Soykan et al. |
| 6,240,317 B1 | 5/2001 | Villaseca et al. |
| 6,250,309 B1 | 6/2001 | Krichen et al. |
| 6,261,230 B1 | 7/2001 | Bardy |
| 6,263,245 B1 | 7/2001 | Snell |
| 6,263,246 B1 | 7/2001 | Goedeke et al. |
| 6,263,247 B1 | 7/2001 | Mueller et al. |
| 6,270,457 B1 | 8/2001 | Bardy |
| 6,289,237 B1 | 9/2001 | Mickle et al. |
| 6,289,238 B1 | 9/2001 | Besson et al. |
| 6,292,698 B1 | 9/2001 | Duffin et al. |
| 6,295,466 B1 | 9/2001 | Ishikawa et al. |
| 6,298,271 B1 | 10/2001 | Weijand |
| 6,300,903 B1 | 10/2001 | Richards et al. |
| 6,304,788 B1 | 10/2001 | Eady et al. |
| 6,319,200 B1 | 11/2001 | Lai et al. |
| 6,329,929 B1 | 12/2001 | Weijand et al. |
| 6,345,203 B1 | 2/2002 | Mueller et al. |
| 6,349,234 B2 | 2/2002 | Pauly et al. |
| 6,363,282 B1 | 3/2002 | Nichols et al. |
| 6,418,346 B1 | 7/2002 | Nelson et al. |
| 6,442,432 B2 | 8/2002 | Lee |
| 6,442,433 B1 | 8/2002 | Linberg |
| 6,477,242 B1 | 11/2002 | Freeny, Jr. |
| 6,480,745 B2 | 11/2002 | Nelson et al. |
| 6,497,655 B1 | 12/2002 | Linberg et al. |
| 6,544,174 B2 | 4/2003 | West et al. |
| 6,738,671 B2 | 5/2004 | Christophersom et al. |
| 6,957,107 B2 | 10/2005 | Rogers et al. |
| 2001/0012955 A1 | 8/2001 | Goedeke et al. |
| 2001/0023360 A1 | 9/2001 | Nelson et al. |
| 2001/0025137 A1 | 9/2001 | Webb et al. |
| 2001/0025189 A1 | 9/2001 | Haueter et al. |
| 2001/0027331 A1 | 10/2001 | Thompson |
| 2001/0027349 A1 | 10/2001 | Eady et al. |
| 2001/0029321 A1 | 10/2001 | Beetz et al. |
| 2001/0031998 A1 | 10/2001 | Nelson et al. |
| 2001/0037056 A1 | 11/2001 | Nunome |
| 2001/0039372 A1 | 11/2001 | Yasushi et al. |
| 2001/0044588 A1 | 11/2001 | Mault |
| 2001/0047125 A1 | 11/2001 | Quy |
| 2001/0051764 A1 | 12/2001 | Bardy |
| 2001/0051787 A1 | 12/2001 | Haller et al. |
| 2002/0013517 A1 | 1/2002 | West et al. |
| 2002/0013518 A1 | 1/2002 | West et al. |
| 2002/0013538 A1 | 1/2002 | Teller |
| 2002/0013613 A1 | 1/2002 | Haller et al. |
| 2002/0013614 A1 | 1/2002 | Thompson |
| 2002/0019584 A1 | 2/2002 | Schulze et al. |
| 2002/0019586 A1 | 2/2002 | Teller et al. |
| 2002/0028988 A1 | 3/2002 | Suzuki et al. |
| 2002/0032470 A1 | 3/2002 | Linberg |
| 2002/0040234 A1 | 4/2002 | Linberg |
| 2002/0052539 A1 | 5/2002 | Haller et al. |
| 2002/0072785 A1 | 6/2002 | Nelson et al. |
| 2002/0082665 A1 | 6/2002 | Haller et al. |
| 2002/0095196 A1 | 7/2002 | Linberg |
| 2002/0109621 A1 | 8/2002 | Khair et al. |
| 2002/0111542 A1 | 8/2002 | Warkentin et al. |
| 2003/0088295 A1 | 5/2003 | Cox |
| 2004/0059205 A1 | 3/2004 | Carlson et al. |
| 2005/0080322 A1 | 4/2005 | Korman |

OTHER PUBLICATIONS

"U.S. Appl. No. 10/328,655, Response filed Feb. 8, 2007 to Non-Final Office Action mailed Nov. 11, 2006", 8 pgs.

"U.S. Appl. No. 10/328,655, Response filed May 9, 2006 to Final Office Action mailed Mar. 14, 2006", 10 pgs.

"U.S. Appl. No. 10/328,655, Response filed Jul. 9, 2007 to Final Office Action mailed May 7, 2007", 16 pgs.

"U.S. Appl. No. 10/328,655 Final Office Action mailed Mar. 14, 2006", 10 pgs.

"U.S. Appl. No. 10/328,655 Final Office Action mailed May 7, 2007", 13 pgs.

"U.S. Appl. No. 10/328,655 Non-Final Office Action mailed Sep. 11, 2006", 12 pgs.

"U.S. Appl. No. 10/328,655 Non-Final Office Action mailed Nov. 1, 2005", 11 pgs.

"U.S. Appl. No. 10/328,655 Notice of Allowance mailed Feb. 14, 2008", 7pgs.

IMPLANTABLE MEDICAL DEVICE HAVING LONG-TERM WIRELESS CAPABILITIES

CROSS REFERENCE TO RELATED APPLICATION

This application is a divisional of U.S. application Ser. No. 10/328,655, filed Dec. 23, 2002, now issued as U.S. Pat. No. 7,395,117, the specification of which is herein incorporated by reference.

TECHNICAL FIELD

This application relates generally to patient management systems, and particularly, but not by way of limitation, to an implantable medical device having long-term wireless capabilities and configured for use in a patient management system.

BACKGROUND OF THE INVENTION

Management of patients with chronic disease consumes a significant proportion of the total health care expenditure in the United States. Many of these diseases are widely prevalent and have significant annual incidences as well. Heart Failure prevalence alone is estimated at over 5.5 million patients in 2000 with incidence rates of over half a million additional patients annually, resulting in a total health care burden in excess of $20 billion. Heart Failure, like many other chronic diseases such as Asthma, Chronic Obstructive Pulmonary Disease ("COPD"), Chronic Pain, and Epilepsy is event driven, where acute de-compensations result in hospitalization. In addition to causing considerable physical and emotional trauma to the patient and family, event driven hospitalizations consume a majority of the total health care expenditure allocated to the treatment of heart failure.

An interesting fact about the treatment of acute de-compensation is that hospitalization and treatment occurs after the event (de-compensation) has happened. However, most Heart Failure patients exhibit prior non-traumatic symptoms, such as steady weight gain, in the weeks or days prior to the de-compensation. If the attending physician is made aware of these symptoms, it is possible to intervene before the event, at substantially less cost to the patient and the health care system. Intervention is usually in the form of a re-titration of the patient's drug cocktail, reinforcement of the patient's compliance with the prescribed drug regimen, or acute changes to the patient's diet and exercise regimens. Such intervention is usually effective in preventing the de-compensation episode and thus avoiding hospitalization.

In order to provide early detection of symptoms that may signal an increased likelihood of a traumatic medical event, patients may receive implantable medical devices that have the ability to measure various body characteristics. For instance, implantable devices are currently available that provide direct measurement of electrical cardiac activity, physical motion, temperature, and other clinical parameters. The data collected by these devices is typically retrieved from the device through interrogation. Alternatively, some implantable medical devices communicate with a repeater located in the patient's home via a short range wireless communications link. While the use of a repeater is convenient for a patient while located near the repeater, no data can be transmitted from the implanted device to the repeater if the implanted device is out of range. This can be extremely inconvenient, and even dangerous, for the patient if a medically significant event occurs while the implanted device is out of range of the repeater. While implantable medical devices having longer-range communications capabilities have been envisioned, these devices have typically been impracticable due to very short battery life.

Patients that have experienced traumatic medical events or that are at high risk of experiencing such events may receive implantable medical devices that can provide therapy. For instance, patients with chronic heart disease can receive implantable cardiac devices such as pacemakers, implantable cardioverter defibrillators ("ICDs"), and HF cardiac resynchronization therapy ("CRT") devices. Typically, Electrophysiologists require their patients to make clinic visits periodically, usually once every three or four months, in order to verify that the implanted device is working correctly and programmed optimally. While some Electrophysiologists welcome this opportunity to perform certain patient specific checks, the vast majority of them require such office visit mainly to perform a device follow-up. This device follow-up is performed regardless of whether any difficulty with the device has been observed. In-person device follow-ups are not popular with Electrophysiologists because theses visits are labor intensive.

Systems have been developed that eliminate the need for in-person device follow-up visits. For instance, trans-telephonic monitoring systems have been developed for wirelessly interrogating the implanted device and transmitting device status information to a remotely located physician via a telephone line. While these systems do not require the patient and the physician to be physically proximate to one another, these systems do require that the patient and the physician be present for the device follow-up at the same time. Moreover, these systems also require that the patient be proximate to the monitoring equipment in order to perform the follow-up. If the patient is away from the location of their monitoring equipment, the remote follow-up is not possible.

Therefore, in light of the above, there is a need for an implantable medical device that has long-range wireless capabilities and that has energy management features that extend battery life to an acceptable level. There is a further need for an implantable medical device that can transmit device status data in a manner that does not require a physician to be present, and that does not require the patient to be proximate to special monitoring equipment, when the status data is transmitted.

SUMMARY OF THE INVENTION

The present invention solves the above-described problems by providing an implantable medical device that has long-range wireless capabilities and long-term battery life. The implantable medical device provided herein is also capable of transmitting status information regarding the operation of the device in a manner that does not require a physician to be present when device status information is transmitted. Moreover, because the wireless telephone network is utilized by the device in one embodiment of the present invention, a patient utilizing the implantable medical device provided herein does not need to be located proximate to special monitoring equipment when the device status information is transmitted. Instead, the patient only needs to be within range of the wireless telephone network.

Generally described, the present invention comprises an implantable medical device that can utilize a pervasive wireless communications network, such as a wireless telephone network or wireless pager network, to directly communicate with a host computer without the need for a repeater device. According to one embodiment of the present invention, the implantable medical device includes a sensor capable of measuring a body characteristic, such as temperature or electrical cardiac activity, and generating clinical data describing the measurement. The implantable medical device also includes a wireless transmitter/receiver unit capable of establishing a communications link with a host computer over a long-range wireless communications network, such as a digital wireless telephone network or personal communication services ("PCS") network. The wireless transmitter/receiver unit is capable of delivering the measured clinical data to the host computer over the wireless network. The host computer may comprise a patient management system, a hospital computer system, or other type of computer system wherein the clinical data is monitored by a health care provider.

In one embodiment of the present invention, power to the wireless transmitter/receiver unit is turned off except when the device is communicating with the host computer. In this manner, the power drain caused by maintaining a traditional wireless transmitter/receiver unit in a "stand by" mode is avoided. Moreover, other features of a traditional wireless receiver/transmitter unit are removed, thereby providing additional power savings. In particular, the wireless transmitter/receiver unit provided herein does not necessarily include a speaker, microphone, display, or keypad. In this manner, significant power savings may be achieved thereby extending the useful life of the implantable medical device provided herein.

According to yet another actual embodiment of the present invention, the implantable medical device provided herein is operative to establish a communications session with a host computer to deliver data for two types of events: regularly scheduled status reports and ad hoc reports for potentially medically significant events. With regard to the ad hoc reports for potentially medically significant events, the implantable medical device is operative to monitor the clinical data generated by the sensor. If the clinical data is determined to be medically significant, the implantable medical device may turn on the wireless transmitter/receiver unit, establish a communications link with a host computer, and transmit the clinical data to the host computer. Once the clinical data has been transmitted to the host computer, the implantable medical device will turn off the wireless transmitter/receiver unit. The clinical data may then be analyzed at the host computer by a physician and appropriate action taken. If the implantable medical device cannot establish a communications link with the host computer or the wireless network, the implantable medical device may store the clinical data in a memory and attempt to deliver the data at a later time when in proximity of a network.

With regard to the regularly scheduled status reports, the implantable medical device is operative to periodically turn on the wireless transmitter/receiver unit, establish a communications link with a host computer via a wireless communications network, and transmit status information regarding the operation and functionality of the device. Additionally, the device may receive software or firmware upgrades from the host computer. Once the scheduled status session has been completed, the device turns the wireless transmitter/receiver unit off, thereby saving power. Status reports may be generated on a predetermined schedule, such as once per day, week, etc.

According to yet another embodiment of the present invention, the implantable medical device also includes a feedback mechanism for providing feedback to a patient in which the device is implanted. The feedback mechanism may comprise a piezoelectric device muscle stimulation, or other type of feedback device for communicating with a patient in which the device is implanted. If data describing the status of the unit or clinical data describing a medically significant event cannot be delivered to the host computer for a predetermined period of time, feedback may be generated by the feedback device in order to indicate to the patient that attention to the device is required.

The present invention also comprises a method of operation for an implantable medical device. These and various other features as well as advantages, which characterize the present invention, will be apparent from a reading of the following detailed description and a review of the associated drawings.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments or examples. These embodiments may be combined, other embodiments may be utilized, and structural, logical, and electrical changes may be made without departing from the spirit and scope of the present invention. The following detailed description is, therefore, not to be taken in a limiting sense, and the scope of the present invention is defined by the appended claims and their equivalents.

The apparatus and methods described herein are described in the context of a patient management system that provides patient management and device management. As used herein, the phrase "patient management" refers to the process of creating and collecting patient specific information, storing and collating the information, and generating actionable recommendations to enable the predictive management of patients with chronic disease. As used herein, the phrase "device management" refers to the process of leveraging a remote communications infrastructure to provide automatic device follow-ups to collect data, provide therapy, and to determine if remote devices are functioning properly. It should be appreciated that although the embodiments of the invention are described in the context of a patient management system, the embodiments of the invention may be utilized within other operating environments. Additional details regarding the patient management system that provides one operating environment for the embodiments of the invention are provided below with respect to FIGS. 2-4B. Additional details regarding the apparatus provided herein are provided below with respect to FIGS. 1 and 5-8.

Figure 1:
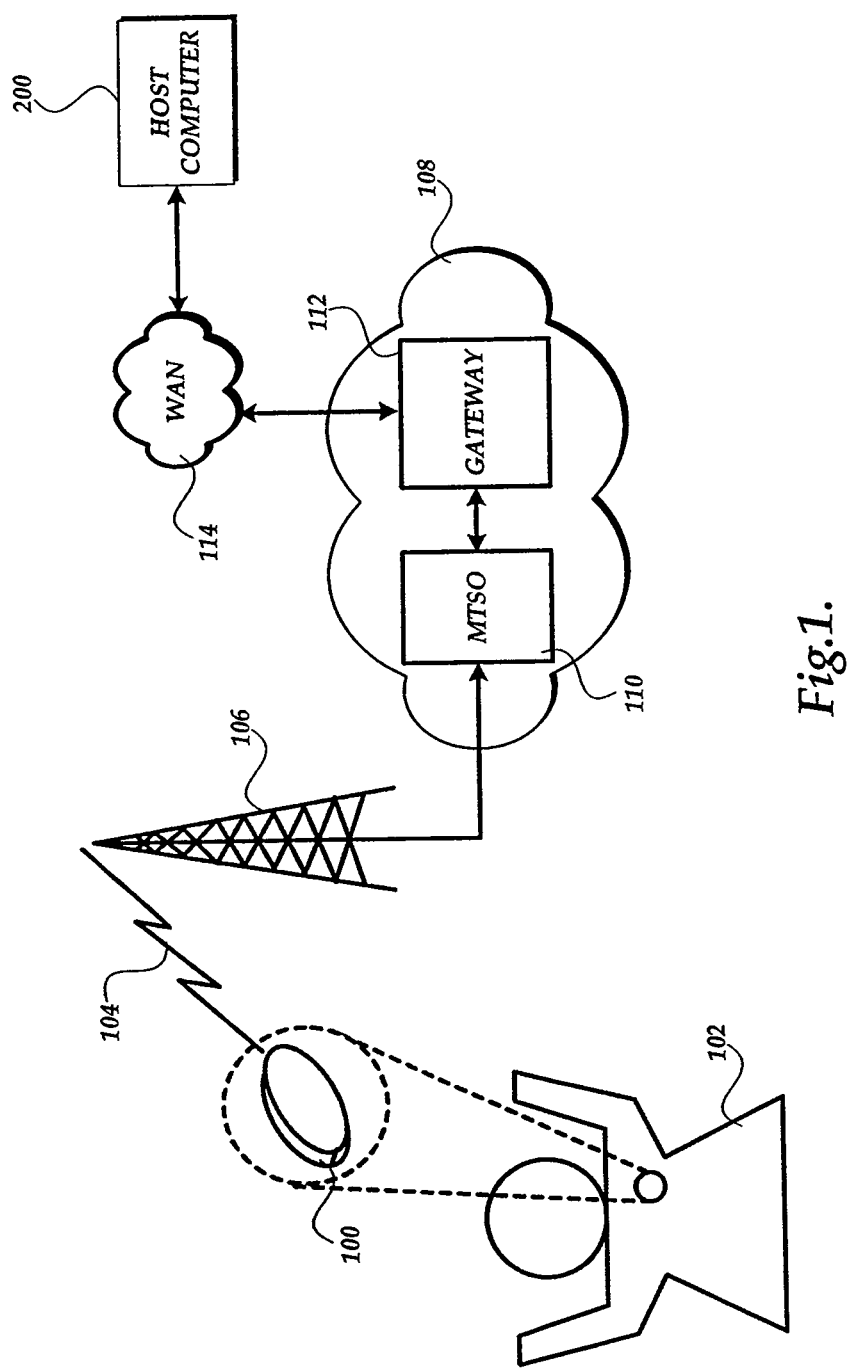
FIG. 1 is a block diagram showing an illustrative operating environment for one actual embodiment of the present invention.

Turning now to FIG. 1, an illustrative operating environment for one actual embodiment of the present invention will be described. As shown in FIG. 1, an implantable medical device 100 is provided that may be implanted within a patient 102. The implantable medical device 100 has the ability to sense and communicate and may also provide therapy. In particular, the implantable medical device 100 includes a sensor which allows it to directly measure characteristics of the patient's body. This may include monitoring electrical cardiac activity, physical motion, temperature, heart rate, activity, blood pressure, breathing patterns, wedge-pressure, ejection fractions, blood viscosity, blood chemistry, blood glucose levels, or other patient specific clinical parameters without any patient compliance.

The implantable medical device 100 provided herein also includes a wireless transmitter/receiver unit capable of establishing a wireless communications link 104 with a long-range wireless network. In an actual embodiment of the present invention, the long-range wireless network comprises a digital wireless telephone network 108. In this embodiment, the implantable medical device 100 communicates directly with a cell tower 106 to establish a communications link to the wireless telephone network 108.

The implantable medical device 100 establishes a connection with the wireless telephone network 108 in the same way that a traditional cellular telephone would establish such a connection and no repeater device is necessary. In particular, the connection is established through a mobile telephone switching office ("MTSO"). A network gateway 112 is also utilized within the wireless telephone network 108 for routing requests to transmit and receive data through a wide area network 114 ("WAN"). In the actual embodiment of the present invention described herein, the WAN 114 comprises the Internet. However, other types of WANs known to those skilled in the art may be utilized.

Through the wireless telephone network 108 and the WAN 114, the implantable medical device 100 can directly establish a data communications link with a host computer 200. The implantable medical device 100 may then send clinical data to the host computer 200 regarding the patient 102. The implantable medical device 100 may also send status information regarding its operation and may receive software or firmware updates and configuration changes from the host computer 200. As will be described in greater detail below with respect to FIGS. 2-4B, the host computer 200 performs a variety of functions within a patient management system in addition to communicating with the implantable medical device 100. Additionally, further details regarding the structure and operation of the implantable medical device 100 will be described below with respect to FIGS. 5-8.

As discussed briefly above, embodiments of the present invention are described with respect to an advanced patient management system configured to collect patient specific information, store and collate the information, and generate actionable recommendations to enable the predictive management of patients. The advanced patient management system is also configured to leverage a remote communications infrastructure to provide automatic device follow-ups to collect data, provide therapy, and to determine if remote devices are functioning properly. The term "patient" is used herein to mean any individual from whom information is collected. The term "caregiver" is used herein to mean any provider of services, such as health care providers including, but not limited to, nurses, doctors, and other health care provider staff.

Figure 2:
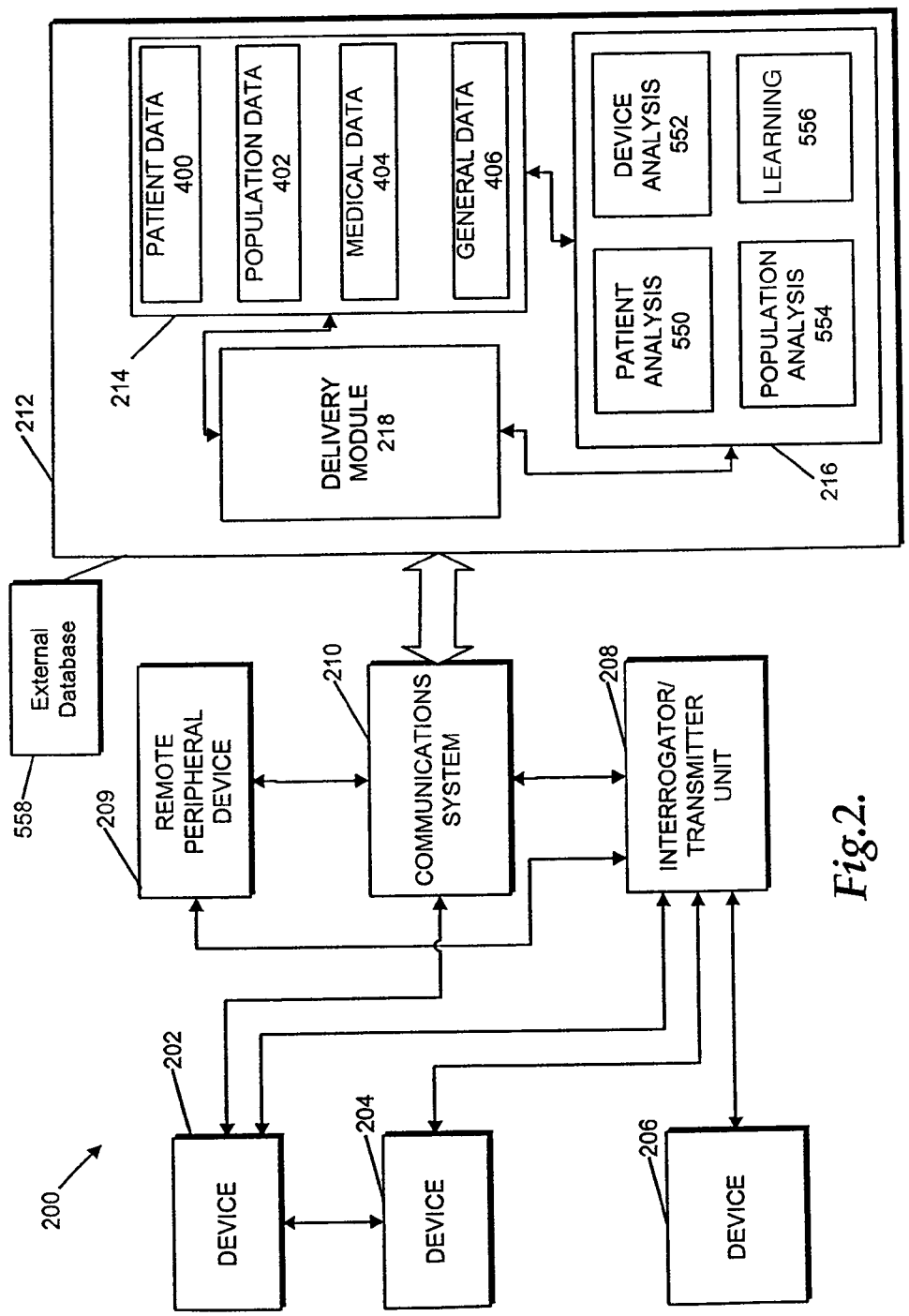
FIG. 2 is a block diagram illustrating an advanced patient management system utilized in one embodiment of the present invention.

FIG. 2 illustrates an example advanced patient management system 200 made in accordance with the present invention. The advanced patient management system 200 can generally include the following components: one or more devices 202, 204, and 206, one or more interrogator/transceiver units 208, a communications system 210, one or more remote peripheral devices 209, and a host 212.

Each component of the advanced patient management system 200 can communicate using the communications system 210. Some components may also communicate directly with one another. For example, devices 202 and 204 may be configured to communicate directly with one another. The various components of the example advanced patient management system 200 illustrated herein are described below.

Devices 202, 204, and 206 can be implantable devices or external devices that may provide one or more of the following functions with respect to a patient: (1) sensing, (2) data analysis, and (3) therapy. For example, in one embodiment, devices 202, 204, and 206 can be implanted or external devices used to measure a variety of physiological, subjective, and environmental conditions of a patient using electrical, mechanical, and/or chemical means. The devices 202, 204, and 206 can be configured to automatically gather data or can require manual intervention by the patient. The devices 202, 204, and 206 can be configured to store data related to the physiological and/or subjective measurements and/or transmit the data to the communications system 210 using a variety of methods, described in detail below. Although three devices 202, 204, and 206 are illustrated in the example embodiment shown, more or fewer devices may be used for a given patient.

The devices 202, 204, and 206 can be configured to analyze the measured data and act upon the analyzed data. For example, the devices 202, 204, and 206 may be configured to modify therapy or provide alarm indications based on the analysis of the data.

In one embodiment, devices 202, 204, and 206 may also provide therapy. Therapy can be provided automatically or in response to an external communication. Devices 202, 204, and 206 can be programmable in that the characteristics of their sensing (e.g., duration and interval), therapy, or communication can be altered via communication between the devices 202, 204, and 206 and other components of the advanced patient management system 200. Devices 202, 204, and 206 can also perform self-checks or be interrogated by the communications system 210 to verify that the devices are functioning properly. Examples of different embodiments of the devices 202, 204, and 206 are provided below.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance.

A heart rhythm sensor, typically found in a pacemaker or defibrillator, is one example of implantable device. In the heart, an electrical wave activates the heart muscle just prior to contraction. As is known in the art, electrical circuits and lead-wires transduce the heart's activation event and reject other, non-essential electrical events. By measuring the time interval between activation events, the heart rhythm can be determined. A transthoracic impedance sensor is another example of an implantable device. During the respiratory cycle, large volumes of air pass into and out of the body. The electrical resistance of the thorax changes markedly as a result of large differences in conductivity of air and body tissues. The thoracic resistance can be measured during respiration and converted into a measurable electrical signal (i.e., impedance) so that breathing rate and profile can be approximated. Implantable devices can also sense chemical conditions, such as glucose levels, blood oxygen levels, etc. Further, the advanced patient management system 200 may utilize other implantable devices as well that provide physiological measurements of the patient, such as drug pumps, neurological devices (e.g., stimulators), oxygen sensors, etc.

Derived measurements can also be determined from the implantable devices. For example, a sleep sensor can rely on measurements taken by an implanted accelerometer that measures body activity levels. The sleep sensor can estimate sleeping patterns based on the measured activity levels. Other derived measurements can include a functional capacity indicator, autonomic tone indicator, sleep quality indicator, cough indicator, anxiety indicator, and cardiovascular wellness indicator for calculating a quality of life indicator for quantifying a patient's overall health and well-being.

Devices 202, 204, and 206 can also be external devices, or devices that are not implanted in the human body, that may be used to measure physiological data. Such devices may include a multitude of devices to measure data relating to the human body, including temperature (e.g., a thermometer), blood pressure (e.g., a sphygmomanometer), blood characteristics (e.g., glucose levels), body weight, physical strength, mental acuity, diet, heart characteristics, and relative geographic position (e.g., a Global Positioning System ("GPS")).

Devices 202, 204, and 206 can also be environmental sensors. The devices can be placed in a variety of geographic locations (in close proximity to patient or distributed throughout a population) and can record non-patient specific characteristics such as, for example, temperature, air quality, humidity, carbon monoxide level, oxygen level, barometric pressure, light intensity, and sound.

One or more of the devices 202, 204, and 206 (for example, device 206) may be external devices that measure subjective or perceptive data from the patient. Subjective data is information related to a patient's feelings, perceptions, and/or opinions, as opposed to objective physiological data. For example, the "subjective" devices can measure patient responses to inquiries such as "How do you feel?" and "How is your pain?" and "Does this taste good?". The device can prompt the patient and record subjective data from the patient using visual and/or audible cues. For example, the patient can press coded response buttons or type an appropriate response on a keypad. Alternatively, subjective data may be collected by allowing the patient to speak into a microphone and using speech recognition software to process the subjective data.

In one example embodiment, the subjective device presents the patient with a relatively small number of responses to each question posed to the patient. For example, the responses available to the patient may include three faces representing feelings of happiness, nominalness, and sadness. Averaged over time, a trend of a patient's well being may emerge with a finer resolution than the quanta of the three responses.

The subjective data can be collected from the patient at set times, or, alternatively, can be collected whenever the patient feels like providing subjective data. The subjective data can also be collected substantially contemporaneously with physiological data to provide greater insight into overall patient wellness.

The device 206 can be any device that accepts input from a patient or other concerned individual and/or provides information in a format that is recognizable to the patient. Device 206 can typically include a keypad, mouse, display, handheld device, interactive TV, a cellular telephone or other radio frequency ("RF") communications device, cordless phone, corded phone, speaker, microphone, email message, and physical stimulus such as an electric shock or change in temperature or light intensity.

Figure 3:
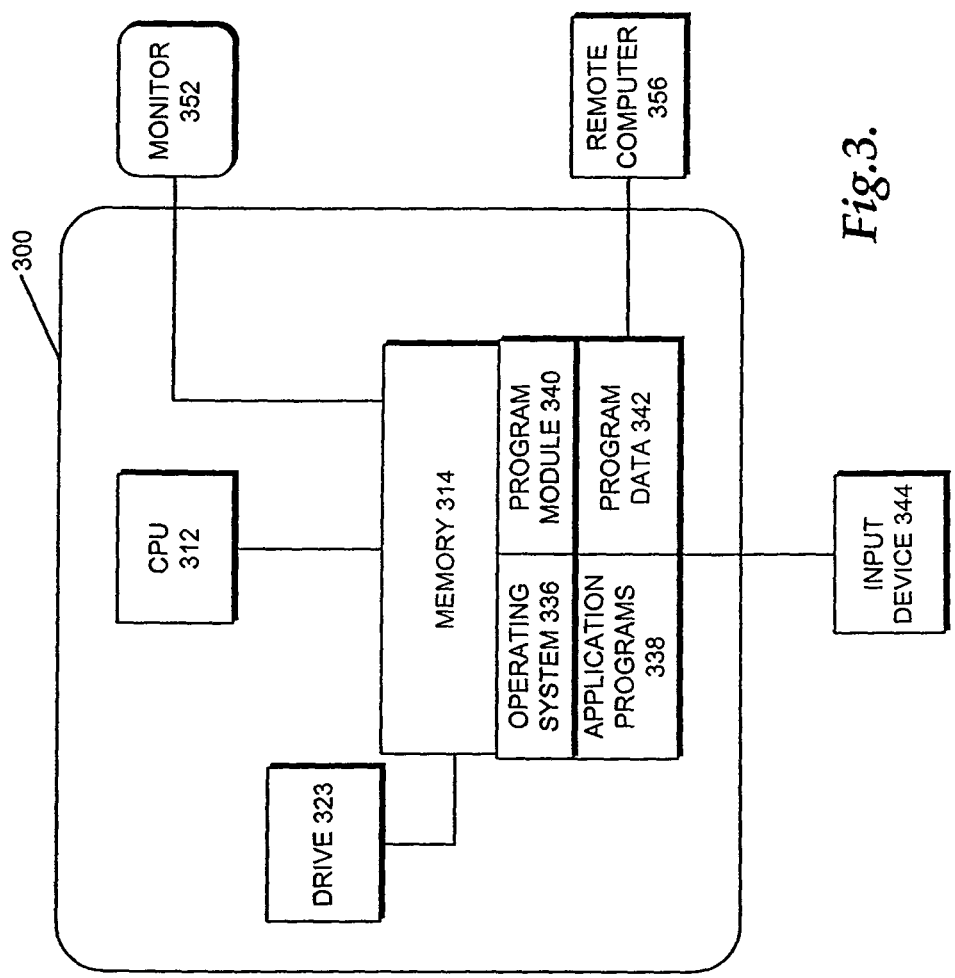
FIG. 3 is a block diagram illustrating a computer system utilized in various embodiments of the present invention.

In one example embodiment, the device 206 includes or is part of a computer system 300, as illustrated in FIG. 3. The computer system 300 can include a central processor unit 312 and a system memory 314. The computer system 300 further includes one or more drives 323 for reading data from and writing data to, as well as an input device 344 such as a keyboard or mouse and a monitor 352 or other type of display device.

A number of program modules may be stored on the drive 323, including an operating system 336, one or more application programs 338, other program modules 340, and program data 342. The computer system 300 may operate in a networked environment using logical connections to one or more remote computers or computer systems 356. Computer system 300 may also comprise a hand-held computer such as a personal digital assistant ("PDA") computer.

Figure 4A:
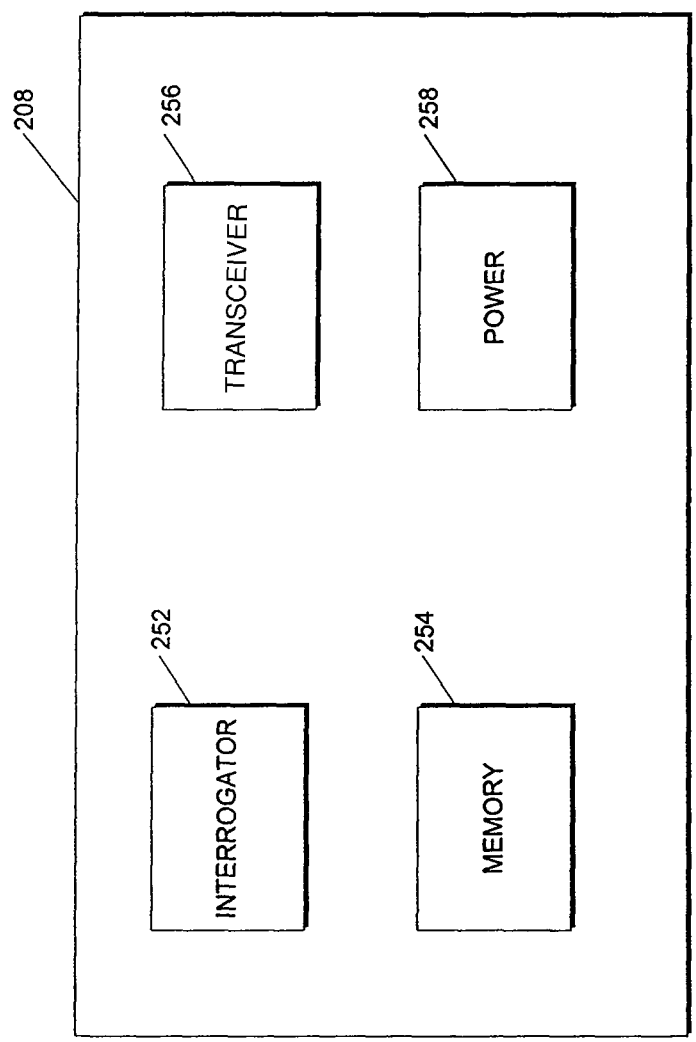
FIG. 4A is a block diagram illustrating an example interrogator/transceiver unit provided by one embodiment of the present invention.

Referring now to FIG. 4A, the advanced patient management system 200 may include one or more interrogator/transceiver units ("ITUs"), such as ITU 208. The ITU 208 includes an interrogator module 252 for receiving data from a device such as devices 202, 204, and 206, a memory module 254 for storing data, a transceiver module 256 for sending data both to the devices 202, 204, and 206 as well as other components of the advanced patient management system 200. The ITU 208 also includes a power module 258 that provides power.

The ITU 208 may perform one or more of the following functions: (1) data storage; (2) data analysis; (3) data forwarding; (4) patient interaction; and (5) patient feedback. For example, the ITU 208 may facilitate communications between the devices 202, 204, and 206 and the communications system 210. The ITU 208 can, periodically or in real-time, interrogate and download into memory clinically relevant patient data from the devices 202, 204, and/or 206. This data can include, in the cardiac sensor context, for example, P and R-Wave measurements, pacing, shocking events, lead impedances, pacing thresholds, battery voltage, capacitor charge times, ATR episodes with electrograms, tachycardia episodes with electrograms, histogram information, and any other clinical information necessary to ensure patient health and proper device function. The data may be sent to the ITU 208 by the devices 202, 204, and 206 in real-time or periodically uploaded out of buffers on the devices.

The ITU 208 may also allow for patient interaction. For example, the ITU 208 may include a patient interface and allow the patient to input subjective data. In addition, the ITU 208 may provide feedback to the patient based on the data that has been analyzed or based on information communicated by the communications system 210.

In another embodiment, the ITU 208 can include a telemetry link from the implanted device to a network that forms the basis of a wireless LAN in the patient's home. The device can systematically download information from the devices 202, 204, and 206 while the patient is sleeping, for example. The data can be transmitted by landline or wirelessly to the communications system 210 or directly to the host 212. In addition, in one embodiment the ITU 208 can function in a hybrid form, utilizing wireless communication when available and defaulting to landline communication when the wireless communication becomes unavailable.

Some devices, such as legacy implanted cardiac rhythm management ("CRM") devices, communicate via an internal telemetry transceiver that communicates with an external programmer. The communication range of such devices is typically 4-12 inches. Communications system 210 may include a special purpose "ITU" that communicates with an implanted legacy device, on one hand, and communicates with the wireless Internet on the other. Patients with legacy devices are provided with these ITUs and are instructed to use them periodically (e.g., monthly).

The ITU 208 may be in the form of a small device that is placed in an inconspicuous place within the patient's residence. Alternatively, the ITU may be implemented as part of a commonly used appliance in the patient's residence. For example, the ITU may be integrated with an alarm clock that is positioned near the patient's bed. In another embodiment, the ITU may be implemented as part of the patient's personal computer system. Other embodiments are also possible.

In another embodiment, the ITU 208 may comprise a hand-held device such as a PDA, cellular telephone, or other similar device that is in wireless communication with the devices 202, 204, and 206. The hand-held device may upload the data to the communications system 210 wirelessly. Alternatively, the hand-held device may periodically be placed in a cradle or other similar device that is configured to transmit the data to the communications system 210.

The ITU 208 can also perform analysis on the data and provide immediate feedback, as well as perform a variety of self-diagnostic tests to verify that it is functioning properly and that communication with the communications system 210 has not be compromised. For example, the ITU 208 can perform a diagnostic loop-back test, which involves sending a request through the communications system 210 to the host 212. The host 212 can then reply with a response back through the communications system 210 to the ITU 208. If a specific duration elapses before the ITU 208 receives the response, or if the ITU 208 receives an unexpected response, the ITU 208 can provide indications that the system is not functioning properly. For example, if wireless communications between the ITU 208 and the communications system 210 have been interrupted, and the ITU 208 performs a self-diagnostic test that fails, the ITU 208 may alert data management service personnel so that corrective action may be taken. Alternatively, the ITU 208 can sound a visual and/or audible alarm to alert the patient that communication has been interrupted. In another embodiment, the ITU 208 can automatically failback to a landline system to communicate with the communications system 210.

In other embodiments of the advanced patient management system 200, the ITU 208 can be eliminated completely, and the devices 202, 204, and 206 can communicate directly with the communications system 210 and/or host 212. For example, device 202 may include a miniature cellular phone capable of wirelessly uploading clinical data from the device on a periodic basis. This is particularly advantageous for devices that are mobile (e.g., an implanted device in a patient that is traveling). The device 202 can incorporate wireless telecommunications such as cellular, BLUETOOTH, or IEEE 802.11B to communicate with the communications system 210.

To conserve the energy of the devices 202, 204, and 206, particularly when the devices (e.g., device 202) are configured to communicate directly with the communications system 210 without using an ITU, in one example embodiment the devices are configured to communicate during a given duty cycle. For example, the device 202 can be configured to communicate with the communications system 210 at given intervals, such as once a week. The device 202 can record data for the time period (e.g., a week) and transmit the data to the communications system 210 during the portion of the cycle that transmission is active and then conserve energy for the rest of the cycle. In another example, the device 202 conserves energy and only communicates with the communications system 210 when an "interesting" event, such as a heart arrhythmia, has occurred. In this manner, device 202 can communicate directly with the communications system 210 and/or host 212 without using the ITU 208, while conserving the energy of the device by communicating only during a given duty cycle.

If multiple devices, such as devices 202, 204, and 206, are provided for a given patient, each device may include its own means for communicating with the ITU 208 or communications system 210. Alternatively, a single telemetry system may be implemented as part of one of the devices, or separate from the devices, and each device 202, 204, and 206 can use this single telemetry system to communication with the ITU 208 or the communications system 210.

In yet another embodiment, the devices 202, 204, and 206 include wires or leads extending from devices 202, 204, and 206 to an area external of the patient to provide a direct physical connection. The external leads can be connected, for example, to the ITU 208 or a similar device to provide communications between the devices 202, 204, and 206 and the other components of the advanced patient management system 200.

The advanced patient management system 200 can also involve a hybrid use of the ITU 208. For example, the a device such as devices 202, 204, and 206 can intelligently communicate via short-range telemetry with the ITU when the patient is located within the patient's home and communicate directly with the communications system 210 or host 212 when the patient is traveling. This may be advantageous, for example, to conserve battery power when the devices are located near an ITU.

Figure 4B:
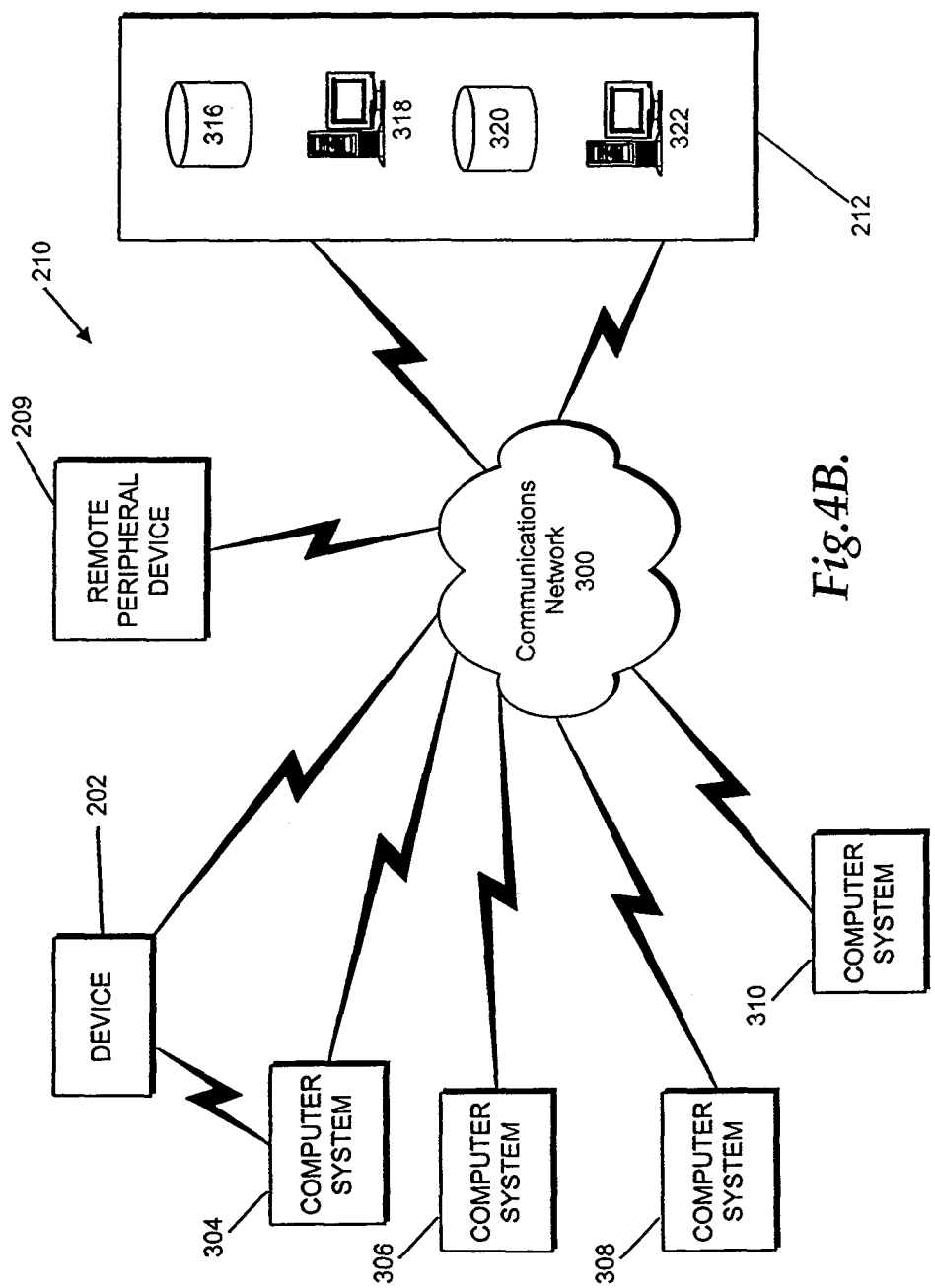
FIG. 4B is a block diagram showing a communication system utilized in one embodiment of the present invention.

Communications system 210 provides for communications between and among the various components of the advanced patient management system 200, such as the devices 202, 204, and 206, host 212, and remote peripheral devices 209. FIG. 4B illustrates communications system 210 according one embodiment of the present invention. The communications system 210 includes a plurality of computer systems 304, 306, 308, and 310, as well as device 202, host 212, and remote peripheral device 109, connect to one another by the communications network 300. The communications network 300 may be, for example, a local area network ("LAN"), wide area network (WAN), or the Internet. Communications among the various components, as described more fully below, may be implemented using wired or wireless technologies.

In the example embodiment illustrated, the host 212 includes server computers 318 and 322 that communicate with computers 304, 306, 308, and 310 using a variety of communications protocols, described more fully below. The server computers 318 and 322 may store information in databases 316 and 320. This information may also be stored in a distributed manner across one or more additional servers.

As shown in FIG. 4B, a variety of communication methods and protocols may be used to facilitate communication between devices 202, 204, and 206, ITU 208, communications system 210, host 212, and remote peripheral device 109. For example, wired and wireless communications may be used. Wired communication methods may include, for example and without limitation, traditional copper-line communications such as DSL, broadband technologies such as ISDN and cable modems, and fiber optics, while wireless communications may include cellular, satellite, radio frequency ("RF"), Infrared, etc.

For any given communication method, a multitude of standard and/or proprietary communication protocols may be used. For example and without limitation, wireless (e.g., radio frequency pulse coding, spread spectrum, direct sequence, time-hopping, frequency hopping, etc.) and other communication protocols (e.g., SMTP, FTP, TCP/IP) may be used. Other proprietary methods and protocols may also be used. Further, a combination of two or more of the communication methods and protocols may also be used.

The various communications between the components of the advanced patient management system 200 may be made securely using several different techniques. For example, encryption and/or tunneling techniques may be used to protect data transmissions. Alternatively, a priority data exchange format and interface that are kept confidential may also be used. Authentication can be implemented using, for example, digital signatures based on a known key structure (e.g., PGP or RSA). Other physical security and authentication measures may also be used, such as security cards and biometric security apparatuses (e.g., retina scans, iris scans, fingerprint scans, veinprint scans, voice, facial geometry recognition, etc.). Conventional security methods such as firewalls may be used to protect information residing on one or more of the storage media of the advanced patient management system 200. Encryption, authentication and verification techniques may also be used to detect and correct data transmission errors.

Communications among the various components of the advanced patient management system 200 may be enhanced using compression techniques to allow large amounts of data to be transmitted efficiently. For example, the devices 202, 204, and 206 may compress the information recorded from the patient prior to transmitting the information to the ITU 208 or directly to the communications system 210. The communication methods and protocols can facilitate periodic and/or real-time delivery of data.

The host 212 may include a database module 214, an analysis module 216, and a delivery module 218 (shown in FIG. 2). The host 212 preferably includes enough processing power to analyze and process large amounts of data collected from each patient, as well as to process statistics and perform analysis for large populations. For example, the host 212 may include a mainframe computer or multi-processor workstation. The host 220 may also include one or more commercial personal computer systems containing sufficient computing power and memory. The host 220 may include storage medium (e.g. hard disks, optical data storage devices, etc.) sufficient to store the massive amounts of high-resolution data that are collected from the patients and analyzed.

The host 212 may also include identification and contact information (e.g., IP addresses and/or telephone numbers) for the various devices communicating with it, such as ITU 208 and peripheral device 209. For example, each ITU 208 may be assigned a hard-coded or static identifier (e.g., IP address, telephone number, etc.), which would allow the host 212 to identify which patient's information the host 212 is receiving at a given instant. Alternatively, each device 202, 204, and 206 may be assigned a unique identification number, or a unique patient identification number may be transmitted with each transmission of patient data.

When a device is first activated, several methods may be used to associate data received by the advanced patient management system 200 with a given patient. For example, each device may include a unique identification number and a registration form that may be filled out by the patient, caregiver, or field representative. The registration form can be used to collect the necessary information to associate collected data with the patient. Alternatively, the user could logon to a web site to allow for the registration information to be collected. Another possible method involves including a barcode on each device that can be scanned prior to or in conjunction with initial measurements to provide information to associate the recorded data with the given patient.

Referring again to FIG. 2, the database module 214 can include a patient database 400, a population database 402, a medical database 404, and a general database 406, all described further below. The patient database 400 includes patient specific data, including data acquired by the devices 202, 204, and 206. The patient database 400 can also include a patient's medical records. The patient database 400 can include historical information regarding the devices 202, 204, and 206. For example, if device 202 is an ICD, the patient database 400 can record the following device information: P and R measurements, pacing frequency, pacing thresholds, shocking events, recharge time, lead impedance, battery voltage/remaining life, ATR episode and EGMs, histogram information, and other device information. The information stored in the database 400 can be recorded at various times depending on the patient requirements or device requirements. For example, the database 400 can be updated at periodic intervals that coincide with the patient downloading data from the device. Alternatively, data in the database 400 can be updated in real time. Typically, the sampling frequency will depend on the health condition being monitored and the co-morbidities.

The population database 402 includes non-patient specific data, such as data relating to other patients and population trends. The population database 402 also records epidemic-class device statistics and patient statistics. The population database 402 also includes data relating to staffing by health care providers, environmental data, pharmaceuticals, etc.

The medical database 404 includes clinical data relating to the treatment of diseases. For example, the medical database 404 can include historical trend data for multiple patients in the form of a record of progression of their disease(s) along with markers of key events.

The general database 406 includes non-medical data of interest to the patient. This can include information relating to news, finances, shopping, technology, entertainment, and sports. The general database 406 can be customized to provide general information of specific interest to the patient. For example, stock information can be presented along with the latest health information as detected from the devices 202, 204, and 206.

In another embodiment, information may also be provided from an external source such as external database 558. For example, the external database may include external medical records maintained by a third party, such as drug prescription records maintained by a pharmacy providing information related to what types of drugs have been prescribed for a patient. The analysis module 216 includes a patient analysis module 550, device analysis module 552, population analysis module 554, and learning module 556.

The patient analysis module 550 may utilize information collected by the advanced patient management system 200, as well as information for other relevant sources, to analyze data related to a patient and provide timely and predictive assessments of the patient's well-being. In performing this analysis, the patient device module 550 may utilize data collected from a variety of sources, include patient specific physiological and subjective data collected by the advanced patient management system 200, medical and historical records (e.g., lab test results, histories of illnesses, etc., drugs currently and previously administered, etc.), as well as information related to population trends provided from sources external to the advanced patient management system 200.

For example, in one embodiment, the patient analysis module 550 may make a predictive diagnosis of an oncoming event based on information stored in the database module 214. For example, the data continuously gathered from a device of a given patient at a heightened risk for a chronic disease event (such as de-compensations in heart failure) can be analyzed. Based on this analysis, therapy, typically device-based or pharmaceutical, can then be applied to the patient.

In another example embodiment, the patient analysis module 550 may provide a diagnosis of patient health status and predicted trend based on present and recent historical data collected from a device as interpreted by a system of expert knowledge derived from working practices within clinics. For example, the patient analysis module 550 may perform probabilistic calculations using currently collected information combined with regularly collected historical information to predict patient health degradation.

In another example embodiment, the patient analysis module 550 may conduct pre-evaluation of the incoming data stream combined with patient historical information and information from patients with similar disease states. The pre-evaluation system is based on data derived from working clinical practices and the records of outcomes. The derived data can be processed into a neural network or equivalent system to reflect the clinical practice. Further, the patient analysis module 550 may also provide means for periodic processing of present and historical data to yield a multidimensional health state indication along with disease trend prediction, next phase of disease progression co-morbidities, and inferences about what other possible diseases may be involved. The patient analysis module 550 may also integrate data collected from internal and external devices with subjective data to optimize management of overall patient health.

The device analysis module 552 analyzes data from the devices 202, 204, and 206 and ITU 208 to predict and determine device failures. For example, if an implanted device 202 fails to communicate at an expected time, device analysis module 552 determines the source of the failure and takes action to restore the performance of the device 202.

The device analysis module 552 may also perform additional deterministic and probabilistic calculations. For example, the device analysis module 552 may gather data related to charge levels within a given device, such as an ICD, and provide analysis and alerting functions based on this information if, for example, the charge level reaches a point at which replacement of the device and/or battery is necessary. Similarly, early degradation or imminent failure of implanted devices can be identified and proactively addressed, or at-risk devices can be closely monitored.

The population analysis module 554 uses the data collected in the database module 214 to manage the health of a population. For example, a clinic managing cardiac patients can access the advanced patient management system 200 and thereby obtain device-supplied advance information to predict and optimize resource allocation both as to immediate care and as a predictive metric for future need of practicing specialists. As another example, the spread of disease in remote populations can be localized and quarantined rapidly before further spread.

In one embodiment, population analysis module 554 trends the patient population therapy and management as recorded by the devices and directs health care resources to best satisfy the needs of the population. The resources can include people, facilities, supplies, and/or pharmaceuticals. In other embodiments, the population analysis module can detect epidemics and other events that affect large population groups. The population analysis module 554 can issue alerts that can initiate a population quarantine, redirect resources to balance size of staffing with number of presenting population, and predict future need of qualified specialists.

The population analysis module 554 may utilize a variety of characteristics to identify like-situated patients, such as, for example, sex, age, genetic makeup, etc. The population analysis module 554 may develop large amounts of data related to a given population based on the information collected by the advanced patient management system 200. In addition, the population analysis module 554 may integrate information from a variety of other sources. For example, the population analysis module 554 may utilized data from public domain databases (e.g. National Institute of Health), public and governmental and health agency databases, private insurance companies, medical societies (e.g. American Heart Association), and genomic records (e.g., DNA sequences).

In one embodiment of the invention, the host 212 may be used as a "data clearinghouse," to gather and integrate data collected from the devices 202, 204, and 206, as well as data from sources outside the advanced patient management system 200. The integrated data can be shared with other interested entities, subject to privacy restrictions, thereby increasing the quality and integration of data available.

The learning module 556 analyzes the data provided from the various information sources, including the data collected by the advanced patient system 200 and external information sources. For example, the learning module 556 analyzes historical symptoms, diagnoses, and outcomes along with time development of the diseases and co-morbidities. The learning module 556 can be implemented via a neural network (or similar) system.

The learning module 556 can be partially trained (i.e., the learning module 556 may be implemented with a given set of preset values and then learn as the advanced patient management system functions) or untrained (i.e., the learning module 556 is initiated with no preset values and must learn from scratch as the advanced patient management system functions). In other alternative embodiments, the learning module 556 may continue to learn and adjust as the advanced patient management system functions (i.e., in real time), or the learning module 556 may remain at a given level of learning and only advanced to a higher level of understanding when manually allowed to do so.

The learning module 556 may implement various algorithms and mathematical modeling such as, for example, trend and statistical analysis, data mining, pattern recognition, cluster analysis, neural networks and fuzzy logic. Learning module 556 may perform deterministic and probabilistic calculations. Deterministic calculations include algorithms for which a clear correlation is known between the data analyzed and a given outcome. For example, there may be a clear correlation between the power left in a battery of an implantable device and the amount of time left before the battery must be replaced.

A probabilistic calculation involves the correlation between data and a given outcome that is less than 200 percent certain. Probabilistic determinations require an analysis of several possible outcomes and an assignment of probabilities for those outcomes (e.g., an increase in weight of a patient may, at a 25% probability, signal an impending de-compensation event and/or indicate that other tests are needed). The learning module 556 may perform probabilistic calculations and select a given response based on less than a 100% probability. Further, as the learning module 556 "learns" for previous determinations (e.g., through a neural network configuration), the learning module 556 may become more proficient at assigning probabilities for a given data pattern, thereby being able to more confidently select a given response. As the amount of data that has been analyzed by the learning module 556 grows, the learning module 556 may become more and more accurate at assigning probabilities based on data patterns. A bifurcated analysis may be performed for diseases exhibiting similar symptoms.

In addition, patient specific clinical information can be stored and tracked for hundreds of thousands of individual patients, enabling a first-level electronic clinical analysis of the patient's clinical status and an intelligent estimate of the patient's short-term clinical prognosis. The learning module 556 may be capable of tracking and forecasting a patient's clinical status with increasing levels of sophistication by measuring a number of interacting co-morbidities, all of which may serve individually or collectively to degrade the patient's health. This will enable learning module 556, as well as caregivers, to formulate a predictive medical response to oncoming acute events in the treatment of patients with chronic diseases such as heart failure, diabetes, pain, cancer, and asthma/COPD, as well as possibly head-off acute catastrophic conditions such as MI and stroke.

In a neural network embodiment, new clinical information is presented to create new neural network coefficients that are distributed as a neural network knowledge upgrade. The learning module 556 can include a module for verifying the neural network conclusions for clinical accuracy and significance. The learning module 556 can analyze a database of test cases, appropriate outcomes and relative occurrence of misidentification of the proper outcomes. In some embodiments, the learning module 556 can update the analysis module 216 when the analysis algorithms exceed a threshold level of acceptable misidentifications.

The delivery module 218 coordinates the delivery of feedback based on the analysis performed by the host 212. In response to the analysis module 216, delivery module 218 can manage the devices 202, 204, and 206, perform diagnostic data recovery, program the devices, and otherwise deliver information as needed.

In some embodiments, the delivery module 218 can manage a web interface that can be accessed by patients or caregivers. The information gathered by an implanted device can be periodically transmitted to a web site that is securely accessible to the caregiver and/or patient in a timely manner. In other embodiments a patient accesses detailed health information with diagnostic recommendations based upon analysis algorithms derived from leading health care institutions.

For example, the caregiver and/or patient can access the data and analysis performed on the data by accessing one or more general content providers. In one example, the patient's health information is accessed through a general portal such as MY YAHOO provided by YAHOO! INC. of Sunnyvale, Calif. A patient can access his or her MY YAHOO homepage and receive information regarding current health and trends derived from the information gathered from the devices 202, 204, and 206, as well as other health information gathered from other sources. The patient may also access information other than health information on the MY YAHOO website, such as weather and stock market information. Other electronic delivery methods such as email, facsimile, etc. can also be used.

In an alternative embodiment, the data collected and integrated by the advanced patient system 200, as well as any analysis performed by the system 200, can be delivered by delivery module 218 to a caregiver's hospital computer system for access by the caregiver. A standard or custom interface can facilitate communications between the advanced patient management system 200 and a legacy hospital system used by the caregiver so that the caregiver can access all relevant information using a system familiar to the caregiver.

In addition, the advanced patient management system 200 can be configured so that various components of the system (e.g., ITU 208, communications system 210, and/or host 212) provide reporting to various individuals (e.g., patient and/or caregiver). For example, different levels of reporting can be provided by (1) the ITU 208 and (2) the host 212. For example, the ITU 208 may be configured to conduct rudimentary analysis of data gathered from devices 202, 204, and 206, and provide reporting should an acute situation be identified. For example, if the ITU 208 detects that a significant heart arrhythmia is imminent or currently taking place, the ITU 208 can provide reporting in the form of an audible or visual alarm.

The host 212 can provide a more sophisticated reporting system. For example, the host 212 may provide exception-based reporting and alerts that categorize different reporting events based on importance. Some reporting events may not require caregiver intervention and therefore can be reported automatically. In other escalating situations, caregiver and/or emergency response personnel may need to become involved. For example, based on the data collected by the advanced patient management system 200, the delivery module 218 can communicate directly with the devices 202, 204, and 206, contact a pharmacy to order a specific medication for the patient, and/or contact 911 emergency response. In an alternative embodiment, the delivery module 218 and/or the patient may also establish a voice communication link between the patient and a caregiver, if warranted.

In addition to forms of reporting including visual and/or audible information, the advanced patient management system 200 can also communicate with and reconfigure one or more of the devices 202, 204, and 206. For example, if device 202 is part of a cardiac rhythm management system, the host 212 and communicate with the device 202 and reconfigure the therapy provided by the cardiac rhythm management system based on the data collected from one or more of the devices 202, 204, and 206. In another embodiment, the delivery module 218 can provide to the ITU 208 recorded data, an ideal range for the data, a conclusion based on the recorded data, and a recommended course of action. This information can be displayed on the ITU 208 for the patient to review.

The advanced patient management system 200 may also include one or more remote peripheral devices 209. The remote peripheral device 209 may include, for example and without limitation, cellular telephones, pagers, PDA devices, facsimiles, remote computers, printers, video and/or audio devices, etc. The remote peripheral device 209 may communicate using landline or wireless technologies and may be used by the patient or caregiver to communicate with the communications system 210 and/or the host 212. For example, the remote peripheral device 209 may be used by a caregiver to receive alerts from the host 212 based on data collected from the patient and to send instructions from the caregiver to either the patient or other clinical staff. In another example, the remote peripheral device 209 may be used by the patient to receive periodic or real time updates and alerts regarding the patient's health and well-being.

Figure 5:
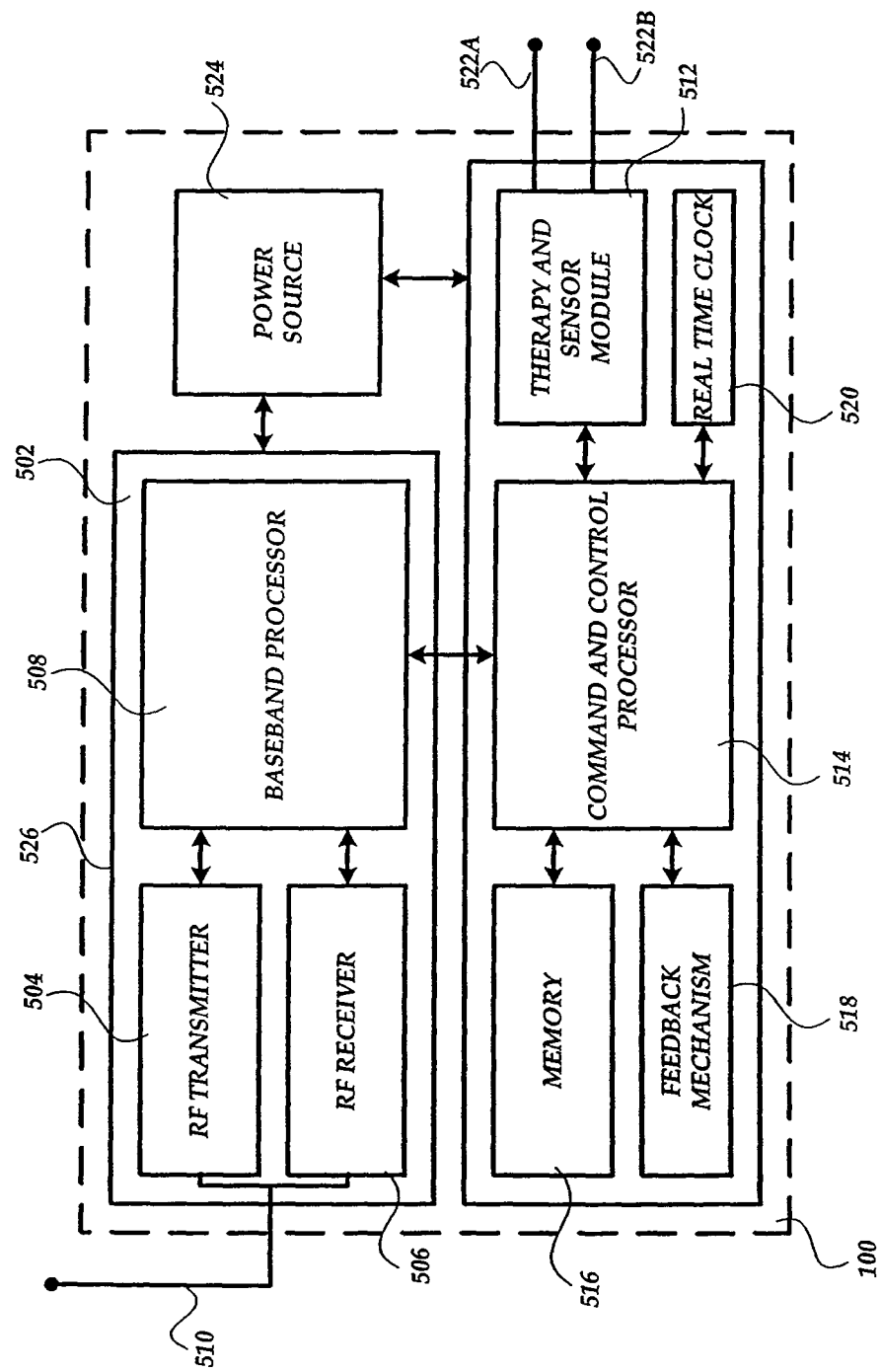
FIG. 5 is a block diagram showing a hardware architecture for an implantable medical device provided according to one actual embodiment of the present invention.

Turning now to FIG. 5, an illustrative hardware architecture for an implantable medical device 100 provided in an actual embodiment of the present invention will be described. As shown in FIG. 5, the implantable medical device 100 comprises a wireless transmitter/receiver unit 502. The wireless transmitter/receiver unit 502 comprises a wireless radio configured to communicate with a wireless telephone system 108. However, the wireless transmitter/receiver unit 502 is configured and operated in a manner that provides the implantable medical device 100 with a long battery life. In particular, as compared to a traditional wireless telephone, the wireless transmitter/receiver unit 502 does not include most of the conventional components that draw power and thereby reduce battery life. The wireless transmitter/receiver unit 502 does not include a display, speaker, keypad, or microphone. As will become apparent from the following discussion, these conventional components are unnecessary in the embodiment of the invention described herein and would only serve to unnecessarily draw power. In order to further conserve power, the implantable medical device 100 removes power from the transmitter/receiver unit 502 except when communicating with the host computer 200. In this manner, the considerable power drain caused by maintaining a transmitter/receiver unit in a "standby" state is avoided. Additional details regarding the power saving features of the implantable medical device 100 will be described below with respect to FIGS. 6-8.

The wireless transmitter/receiver unit 502 provided herein comprises a radio frequency ("RF") transmitter 504, an RF receiver 506, a baseband processor 508, and an antenna 510. As known to those skilled in the art, the RF receiver 506 and the RF transmitter 504 are responsible for receiving and transmitting signals, respectively, to and from the wireless telephone network 108. The baseband processor 508 is responsible for negotiating channel frequencies with the wireless telephone network 108 and for performing other tasks necessary to establish and maintain a valid communications channel with the wireless telephone network 108. The wireless transmitter/receiver unit 502 may be encased in a shield 526. In one embodiment of the present invention, the wireless transmitter/receiver unit 502 may comprise a dual-mode wireless transceiver for operation under several wireless telephone standards. In this manner, communication may be made with a wireless telephone network regardless of the wireless standard in use where the patient is currently located. Conventional wireless transmitters, receivers, and baseband processors are well known to those skilled in the art.

The implantable medical device 100 also comprises a command and control processor 514. The processor 514 controls the operation of the implantable medical device 100, including communicating with the host computer 200, performing power management functions such as turning the wireless transmitter/receiver unit 502 on and off appropriately, receiving and analyzing clinical data generated by the therapy and sensor 512, instructing the feedback mechanism 518 to generate feedback for a patient, applying software, firmware, and configuration changes received from the host computer 200, and other functions. The processor 514 comprises a microprocessor-based computer, which may include one or more processing units and a memory 516, suitable for use in an implantable medical device. Such processors are known to those skilled in the art.

As briefly described above, the implantable medical device 100 also comprises a therapy and sensor module 512 capable of measuring a body characteristic and generating clinical data describing the measurement. One type of therapy and sensor module 512, is a heart rhythm sensor, typically found in a pacemaker or defibrillator. In the heart, an electrical wave activates the heart muscle just prior to contraction. As is known in the art, electrical circuits contained within the therapy and sensor module 512 and lead-wires 522A-B detect the heart's activation event and reject other, non-essential electrical events. By measuring the time interval between activation events, the heart rhythm can be determined.

Another example of a therapy and sensor module 512 is an activity sensor. Physical motion of an object (e.g. human body) can be detected by measuring the acceleration (i.e. rate velocity change). The acceleration can be measured along one axis, two axes, or in three dimensions. An accelerometer converts acceleration into a measurable electrical signal.

In an embodiment of the present invention, an activity sensor may be utilized to manually turn the wireless transmitter/receiver 502 on and off. For instance, the processor 514 may be programmed to turn off the wireless transmitter/receiver 502 if the activity sensor detects a predefined number of consecutive pulses. The pulses may be generated by the patient tapping in a controlled pattern on their chest near the location of the implantable medical device 100. In this manner, the radio frequency generating aspects of the implantable medical device 100 may be discontinued while a patient is on an airplane or in another location sensitive to radio frequency generation. The patient may return the device 100 to normal operation using a similar method. A similar method may also be used to initiate an emergency transmission.

A transthoracic impedance sensor is another example of a therapy and sensor module 512. During the respiratory cycle, large volumes of air pass in and out of the body. The electrical resistance of the thorax changes markedly as a result of large differences in conductivity of air and body tissues. The thoracic resistance can be measured during respiration and thus respiration is converted into a measurable electrical signal (impedance).

A core body temperature sensor is another example of a therapy and sensor 512 module that may be used in the implantable medical device 100. Electrical characteristics of materials are modulated by temperature. The measurement of electrical signals proportional to temperature can permit absolute temperature measurement within an implanted device.

The therapy and sensor 512 module may also provide therapy. Therapy can be provided automatically or in response to an external communication from the host computer 200. The therapy and sensor 512 module can be programmable in that the characteristics of their sensing (e.g., duration, interval), therapy, or communication can be altered via communication received from the host computer 200. The therapy and sensor 512 module can also perform self-checks or be interrogated by the processor 514 to determine if it is functioning properly. It should be appreciated that the therapy and sensor 512 module described herein are merely illustrative and that other types of sensors may be utilized. Moreover, derived measurements may also be determined from the sensors. For example, a sleep sensor can rely on measurements taken by an implanted accelerometer.

As described briefly above, the implantable medical device 100 may also include a feedback mechanism 518. The feedback mechanism 518 may comprise a piezoelectric audio device, pager motor, or other type of device for providing a low-intensity muscle stimulation to a patient. In this manner, the feedback mechanism 518 may notify the patient of a malfunction of the device 100 or serious medical condition. A real time clock 520 is also provided for synchronizing the activities of the device 100 with those of the host computer 200. The real time clock 520 may be set based upon data received from the host computer 200 or other type of network time server.

The antenna 510 utilized in the implantable medical device 100 is a physiologically appropriate antenna that is mounted conformal to the packaging of the device 100. In one embodiment of the present invention, the implantable medical device 100 is electrically divided in half, thereby creating two dipole halves that may be differentially driven to create an antenna effect. Alternatively, the lead-wires 522A-B may be utilized in place of the antenna 510.

The operation of the device 100 is powered by a high power density power source 524 suitable for use in an implantable medical device and having power characteristics suitable for driving the wireless transmitter/receiver unit 502 for an appropriate period of time. An appropriate rechargeable power source may also be utilized as may an alternative power source, such as a miniature fuel cell.

Figure 6:
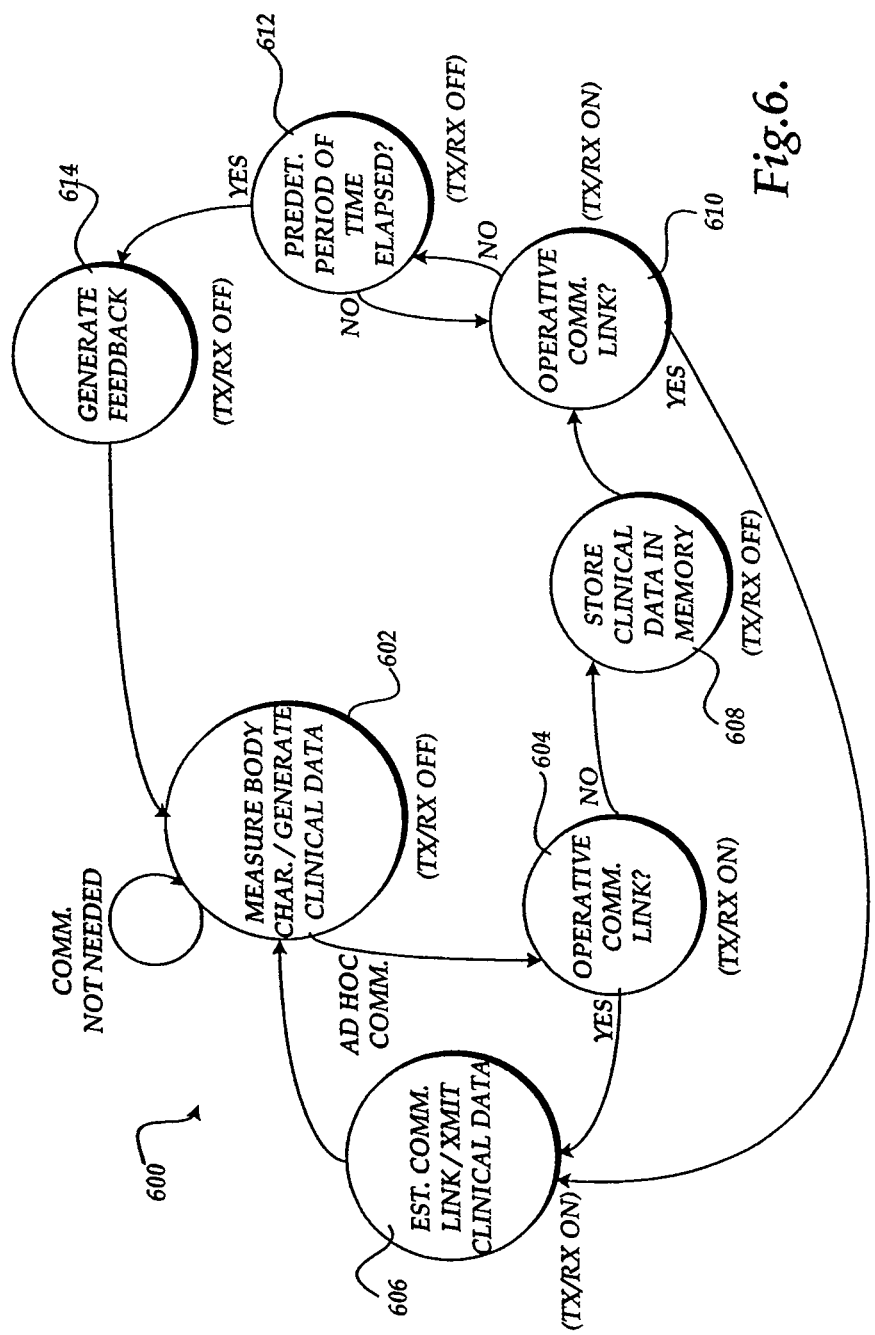
FIG. 6 is a state diagram illustrating a method of operation for an implantable medical device in one embodiment of the present invention.

Referring now to FIG. 6, a state machine 600 showing an illustrative method of operation for the implantable medical device 100 will be described. The state machine 600 begins its operation at state 602, where the therapy and sensor 512 module measures the appropriate body characteristic and generates clinical data describing the characteristic. The clinical data is transmitted from the sensor to the processor 514 for analysis. The processor 514 analyzes the clinical data and determines if the data should be transmitted to the host computer 200. In this regard, the processor 514 may be programmed to determine if the clinical data relates to a potentially medically significant event. If no clinical data is received from the sensor that appears to be related to a medically significant event, the state machine 600 remains at state 602, where clinical data generated by the therapy and sensor 512 module is continually analyzed. Additionally, the wireless transmitter/receiver unit 502 is turned off while the device 100 is operating in state 602.

If, in state 602, the processor 514 determines that clinical data has been received from the therapy and sensor 512 module that should be sent to the host computer 200 for processing, the state machine 600 transitions to state 604. At state 604, the wireless transmitter/receiver unit 502 is periodically turned on so that a determination can be made as to whether a communications link with the host computer 200 may be established. If a communications link with the host computer 200 can be established, the state machine 600 transitions from state 604 to state 606. At state 606, the communications link with the host computer 200 is established and the processor 514 transmits the clinical data to the host computer 200. While the communications session is established between the device 100 and the host computer 200, the host computer 200 may also transmit software or firmware updates, or configuration changes. Likewise, the processor 514 may also transmit status information regarding the operation of the device 100. Once the communications have been completed, the communications link is closed and the transmitter/receiver unit 502 is turned off. The state machine 600 then transitions from state 606 back to state 602, described above.

If, at state 604, the processor 514 determines that an operative communication link cannot be established with the host computer 200, the state machine 600 transitions to state 608.

At state 608, the clinical data is stored in the memory 516 for future delivery to the host computer 200. The wireless transmitter/receiver unit 502 is also turned off. From state 608, the state machine 600 transitions to state 610, where the wireless transmitter/receiver unit 502 is periodically turned on to determine whether a communications link with the host computer 200 can be established. If a communications link can be established, the state machine 600 transitions from state 610 to state 606, where the clinical data is delivered to the host computer 200.

If, at state 610, a communications link cannot be established with the host computer 200, the state machine 600 transitions to state 612. At state 612, the wireless transmitter/receiver unit 502 is turned off. Additionally, a determination is made by the processor as to whether a predetermined amount of time has elapsed since the last time a connection was established with the host computer 200. If the predetermined period of time has not elapsed, the state machine 600 transitions back to state 610 where another determination is made as to whether a communications link can be established. If the predetermined period of time has elapsed, the state machine 600 transitions to state 614, where the wireless transmitter/receiver unit 502 is turned off and the feedback mechanism 518 is instructed to generate feedback to the patient. In this manner, the patient may be notified if a communications link with the host computer 200 has been unavailable for a period of time. From state 614, the state machine 600 transitions back to state 602, described above.

Figure 7:
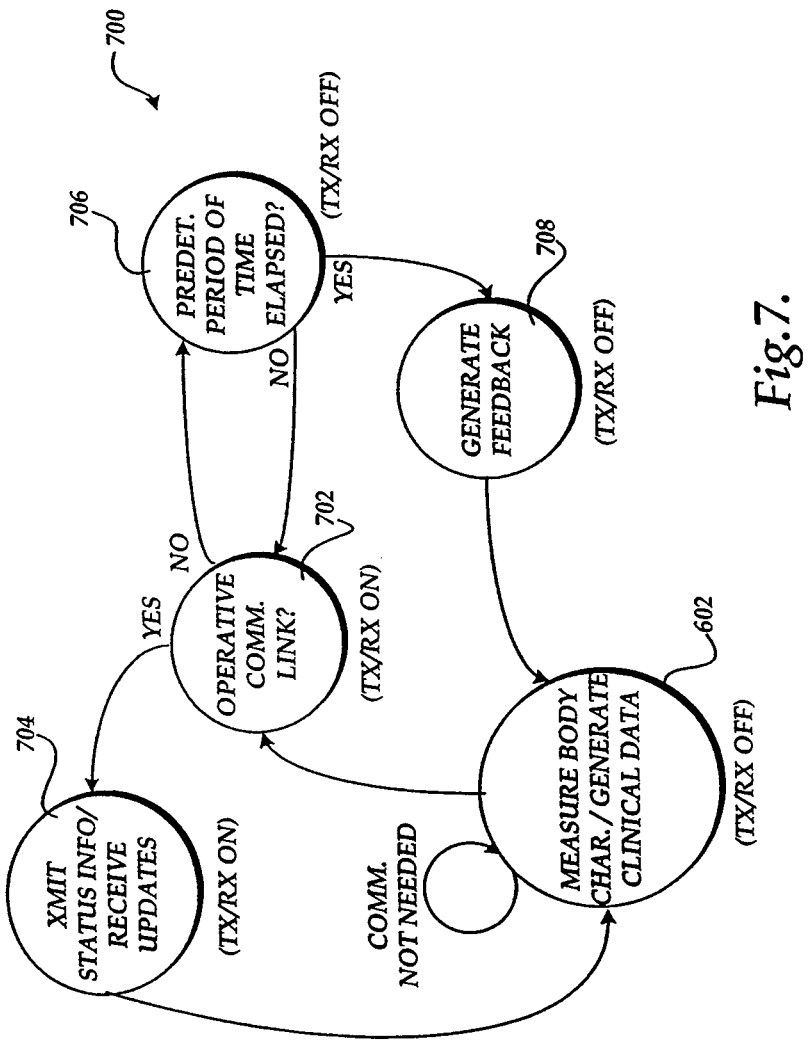
FIGS. 7 and 8 are state diagrams illustrating additional aspects of a method of operation for an implantable medical device in several embodiments of the present invention.

Referring now to FIG. 7, additional aspects of the method of operation for the implantable medical device 100 will be described. In particular, FIG. 7 shows a state machine 700 that describes an aspect of the method of operation for the device 100 wherein status information regarding the operation of the device 100 is periodically transmitted to the host computer 200. Moreover, software and firmware updates and configuration changes may be received from the host computer 200 during this process.

The state machine 700 begins its operation at state 602, where the therapy and sensor 512 module measures the appropriate body characteristic and generates clinical data describing the characteristic. As described above, the clinical data is transmitted from the sensor to the processor 514 for analysis. The processor 514 analyzes the clinical data and determines if the data should be transmitted to the host computer 200. Additionally, during this processing, the processor 514 also determines whether a communications session should be established with the host computer 200 to deliver status information regarding the operation of the device 100. In this regard, the processor 514 may be programmed to periodically deliver status information to the host computer 200. For instance, status information may be delivered on a daily, weekly, or monthly basis. In addition to allowing the host computer 200 to confirm the proper operation of the device 100, the periodic communications sessions also allow the device 100 to confirm the existence of a valid communications link with the wireless telephone network 108.

If, at state 602, the processor determines that a periodic status report should be transmitted to the host computer 200, the state machine 700 transitions to state 702. At state 702, the wireless transmitter/receiver unit 502 is periodically turned on so that a determination can be made as to whether a communications link with the host computer 200 may be established. If a communications link with the host computer 200 can be established, the state machine 700 transitions from state 702 to state 704. At state 704, the communications link with the host computer 200 is established and the processor 514 transmits the status data to the host computer 200. While the communications session is established between the device 100 and the host computer 200, the host computer 200 may also transmit software or firmware updates, or configuration changes. Once the communications have been completed, the communications link is closed and the transmitter/receiver unit 502 is turned off. The state machine 700 then transitions from state 704 back to state 602, described above. The wireless transmitter/receiver unit 502 is turned off while the device 100 is operating in state 602.

If, at state 702, the processor 514 determines that an operative communication link cannot be established with the host computer 200, the state machine 700 transitions to state 706. At state 706, a determination is made by the processor as to whether a predetermined amount of time has elapsed since the last time a connection was established with the host computer 200. If the predetermined period of time has not elapsed, the state machine 700 transitions back to state 702 where another determination is made as to whether a communications link can be established. If the predetermined period of time has elapsed, the state machine 700 transitions to state 708, where the wireless transmitter/receiver unit 502 is turned off and the feedback mechanism 518 is instructed to generate feedback to the patient. In this manner, the patient may be notified if a communications link with the host computer 200 could not be established for a period of time. From state 708, the state machine 700 transitions back to state 602, described above.

Figure 8:
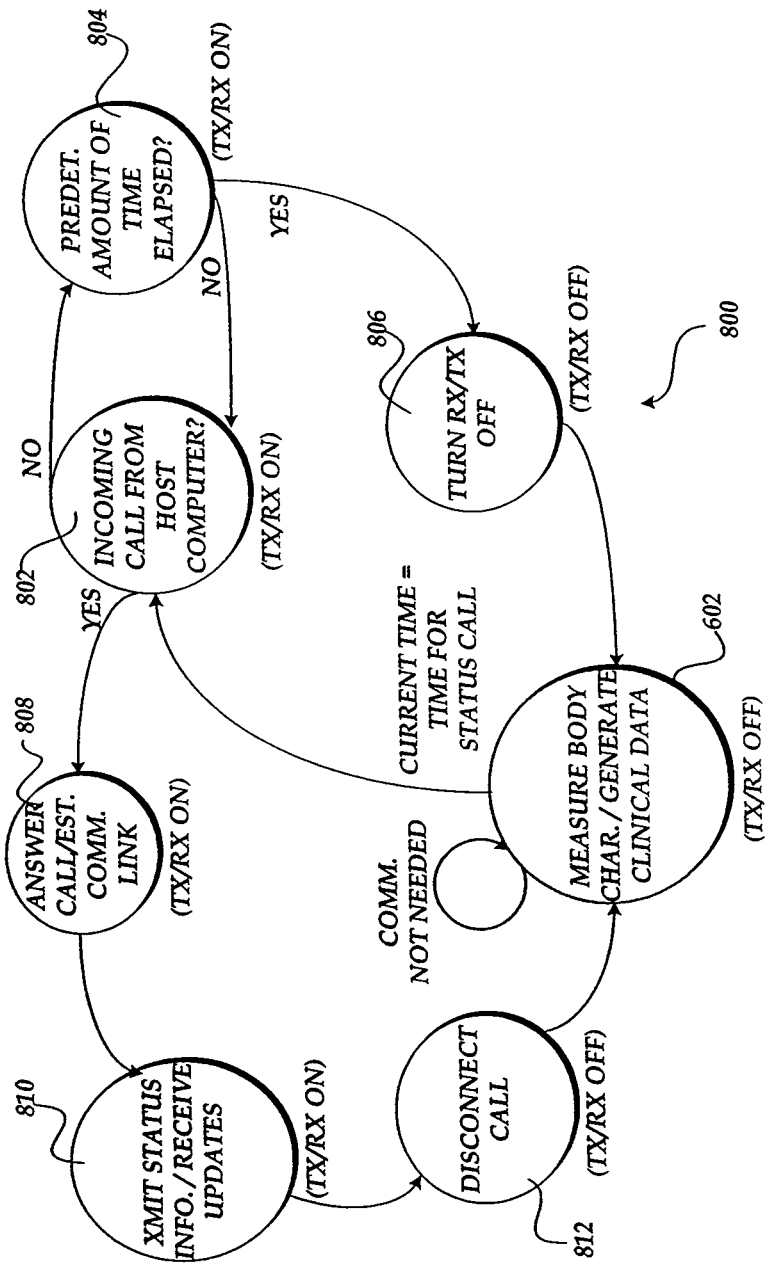

Turning now to FIG. 8, an embodiment of the invention will be described in which the device 100 is operative to receive incoming telephone calls from the host computer 200. To allow the device 100 to accept incoming calls from the host computer 200 while still conserving power, the processor 514 is programmed to turn the wireless transmitter/receiver unit 502 on at a predetermined time and for a predetermined period of time. For instance, the wireless transmitter/receiver unit 502 may be turned on at 3:00 a.m. for several minutes. The predetermined period of time is coordinated with the host computer 200.

If an incoming call is received from the host computer 200 during the time the wireless transmitter/receiver unit 502 is turned on, an exchange of data between the device 100 and the host computer 200 takes place. If no incoming call is received at the device 100 within the predetermined period of time, the processor 514 turns the wireless transmitter/receiver unit 502 off until the next occurrence of the predetermined time. By making itself available for incoming calls at a predetermined time, the device 100 can receive incoming calls from the host computer 200 and conserve energy by only remaining in a standby mode for a predetermined period of time. The state machine 800 illustrates this process.

The state machine 800 begins its operation at state 602, where the therapy and sensor 512 module measures the appropriate body characteristic and generates clinical data describing the characteristic. As described above, the clinical data is transmitted from the sensor to the processor 514 for analysis. The processor 514 analyzes the clinical data and determines if the data should be transmitted to the host computer 200. Additionally, during this processing, the processor 514 also determines whether the current time as specified by the real time clock 520 is the time at which the wireless transmitter/receiver unit 502 should be turned on for incoming calls. If the current time is not the time to turn on the wireless transmitter/receiver unit 502, the state machine 800 remains in state 602. The wireless transmitter/receiver unit 502 is turned off while in state 602.

If, at state 602, the processor 514 determines that the current time is the predetermined time at which the wireless transmitter/receiver unit 502 should be turned on for receiving calls, the state machine 800 transitions to state 802. At state 802, the wireless transmitter/receiver unit 502 is turned on and placed in a standby mode for receiving incoming calls. At state 802, a determination is also made as to whether an incoming call from the host computer 802 has been received. If an incoming call is not received, the state machine 800 transitions to state 804, where a determination is made as to whether a predetermined period of time has elapsed since the wireless transmitter/receiver unit 502 was turned on. If a predetermined time has not elapsed, the state machine 800 returns to state 802. If a predetermined time has elapsed, the state machine 800 transitions to state 806, where the wireless transmitter/receiver unit 502 is turned off. The state machine then transitions from state 806 back to state 602.

If, at state 802, an incoming call from the host computer 200 is detected, the state machine transitions to state 808. At state 808, the incoming call is answered and a communications link is established between the device 100 and the host computer 200 over the wireless telephone network 108. The state machine 800 then transitions to state 810. At state 810, a communications session between the device 100 and the host computer 200 takes place. During the communications session, the device 100 may transmit status information or clinical data to the host computer 200. The host computer 200 may also send software or firmware updates, configuration changes, and other data to the device 100.

Once the communications session between the host computer 200 and the device 100 has been completed, the state machine 800 transitions from state 810 to state 812. At state 812, the telephone call is disconnected and the wireless transmitter/receiver unit 502 is turned off. The state machine 800 similarly transitions to state 812 if the call is disconnected inadvertently during the communications session. From state 812, the state machine 800 returns to state 602, described above.

Based upon the foregoing, it should be appreciated that the present invention provides an implantable medical device having long-range and long-term wireless capabilities. Although the invention has been described in language specific to computer structural features, methodological acts and by computer readable media, it is to be understood that the invention defined in the appended claims is not necessarily limited to the specific structures, acts or media described. Therefore, the specific structural features, acts and mediums are disclosed as exemplary embodiments implementing the claimed invention. Since many embodiments of the invention can be made without departing from the spirit and scope of the invention, the invention resides in the claims hereinafter appended.

We claim:

1. A method of operation for an implantable medical device comprising a processor, a sensor, and a wireless transmitter/receiver unit, the method comprising:
   obtaining a measurement of a body characteristic at the sensor and generating clinical data describing the measurement;
   determining whether said clinical data relates to a medically significant event; and
   in response to determining that said clinical data relates to said medically significant event, then:
      turning on said transmitter/receiver unit to establish a direct wireless telephone communications link between said transmitter/receiver unit and a host computer;
      transmitting said clinical data or status information regarding the operation of said implantable medical device to said host computer via said wireless telephone communications link; and turning said transmitter/receiver unit off after said clinical data or status information has been transmitted to said host computer.

2. The method of claim 1, comprising:

determining whether an external local transceiver is within a short-range telemetry communication range of said implantable wireless transmitter/receiver unit;

establishing a first communications link with said host computer using said external local transceiver, when said wireless transmitter/receiver unit is within said short-range telemetry communication range of said external local transceiver, to deliver said clinical data to said host computer using said first communications link; and establishing a second communications link with said host computer over a pervasive wireless communications network, when said wireless transmitter/receiver unit is not within said short-range telemetry communication range of said external local transceiver, to deliver said clinical data to said host computer over said second communications link.

3. The method of claim 1, comprising:

determining whether said communications link with said host computer is operative before delivering said clinical data; and in response to determining that said communications link is not operative, storing said clinical data in a memory until said communications link becomes operative.

4. The method of claim 3, comprising:

determining whether said clinical data stored in said memory has not been delivered to said host computer within a specified period of time; and in response to determining that said clinical data has not been delivered, alerting a patient in which said implantable medical device is implanted.

5. The method of claim 3, comprising:

determining whether said communications link cannot be established with said host computer for a specified period of time; and in response to determining that said communications link has not been established, alerting a patient in which said implantable medical device is implanted.

6. The method of claim 1, comprising:

recurrently establishing said communications link with said host computer to transmit status information regarding operation of said implantable medical device to said host computer or to receive a software update or a firmware update from said host computer.

7. The method of claim 1, wherein turning on said transmitter/receiver unit comprises turning on said transmitter/receiver unit for a specified period of time.

8. The method of claim 1, wherein said body characteristic comprises at least one of electrical cardiac activity, physical motion, temperature, heart rate, activity, blood pressure, breathing pattern, wedge-pressure, ejection fraction, blood viscosity, blood chemistry, or blood glucose level.

9. The method of claim 1, wherein said implantable medical device comprises an activity sensor to detect activity, and wherein said method comprises:

detecting a predefined number of consecutive pulses; and at least one of:

activating said wireless transmitter/receiver unit when said wireless transmitter/receiver unit is inactive; or deactivating said wireless transmitter/receiver unit when said wireless transmitter/receiver unit is active.

10. The method of claim 1, wherein said implantable medical device comprises an activity sensor to detect activity, and wherein said method comprises:

detecting a predefined number of consecutive pulses;

in response to detecting said predefined number of consecutive pulses:

turning on said transmitter/receiver unit;

establishing an emergency communications link with said host using said wireless transmitter/receiver unit; and transmitting said clinical data to said host computer over said emergency communications link.

11. The method of claim 1, wherein turning on said transmitter/receiver unit establishing said wireless telephone communications link comprises accessing a wireless telephone network without use of a repeater device.

12. A method of operation for an implantable medical device comprising a processor, a sensor, and a wireless transmitter/receiver unit, the method comprising:

obtaining a measurement of a body characteristic at the sensor and generating clinical data describing the measurement;

turning on said transmitter/receiver unit at a specified time;

determining whether an incoming wireless telephone call is received directly from a host computer at said transmitter/receiver unit from a host computer while said transmitter/receiver unit is turned on, the received wireless telephone call establishing a direct communications link;

in response to determining that said incoming wireless telephone call has been received at said transmitter/receiver unit from said host computer, transmitting said clinical data or status information regarding the operation of said implantable medical device to said host computer, and turning said transmitter/receiver unit off after said status information has been transmitted to said host computer;

determining whether said clinical data has not been delivered to said host computer within a predetermined period of time; and in response to determining that said clinical data has not been delivered, alerting a patient in which said implantable medical device is implanted.

13. The method of claim 12, comprising:

determining whether an external local transceiver is within a short-range telemetry communication range of said implantable wireless transmitter/receiver unit;

establishing a first communications link with said host computer using said external local transceiver, when said wireless transmitter/receiver unit is within said short-range telemetry communication range of said external local transceiver, to deliver said clinical data to said host computer using said first communications link; and establishing a second communications link with said host computer over a pervasive wireless communications network, when said wireless transmitter/receiver unit is not within said short-range telemetry communication range of said external local transceiver, to deliver said clinical data to said host computer over said second communications link.

* * * * *